US007219555B2

(12) United States Patent
Salvesen

(10) Patent No.: US 7,219,555 B2
(45) Date of Patent: May 22, 2007

(54) METHOD AND APPARATUS FOR TESTING A JOINT REPLACEMENT DEVICE

(76) Inventor: William R. Salvesen, 10 Point Pleasant Rd., Hopatcong, NJ (US) 07083

( * ) Notice: Subject to any disclaimer, the term of this patent is extended or adjusted under 35 U.S.C. 154(b) by 124 days.

(21) Appl. No.: 11/116,518

(22) Filed: Apr. 28, 2005

(65) Prior Publication Data

US 2005/0241404 A1    Nov. 3, 2005

Related U.S. Application Data

(60) Provisional application No. 60/567,484, filed on May 3, 2004.

(51) Int. Cl.
*A61F 2/38* (2006.01)
(52) U.S. Cl. .................... 73/788; 73/804; 73/865.1; 73/865.3
(58) Field of Classification Search .................. 73/788, 73/865.1, 865.3, 804
See application file for complete search history.

(56) References Cited

U.S. PATENT DOCUMENTS

| 4,901,580 A | * | 2/1990 | Potts ........................... 73/788 |
| 5,259,249 A | * | 11/1993 | Fetto ........................... 73/794 |
| 5,342,362 A | * | 8/1994 | Kenyon et al. ............... 606/79 |
| 6,058,784 A | * | 5/2000 | Carroll et al. ................ 73/856 |
| 6,491,273 B2 | * | 12/2002 | King et al. ............... 248/276.1 |
| 6,554,837 B1 | * | 4/2003 | Hauri et al. .................. 606/87 |
| 6,865,954 B2 | * | 3/2005 | Zubok et al. ................ 73/804 |
| 7,040,177 B2 | * | 5/2006 | Zubok et al. ................ 73/804 |

* cited by examiner

*Primary Examiner*—Edward Lefkowitz
*Assistant Examiner*—Freddie Kirkland, III
(74) *Attorney, Agent, or Firm*—Arthur Jacob

(57) ABSTRACT

An apparatus and method for testing components of a joint replacement device in desired articulation relative to one another under a load, include: a first unit or step operable to impart undulating orientations of a first member of the joint replacement device; and a second unit or step operable to locate a second member of the joint replacement device proximate to the first member of the joint replacement device such that an articulation surface of the second member engages an articulation surface of the first member for movement in response to the undulating orientations of the first member, wherein at least one of: (i) the second unit is operable to automatically adjust the location of the second member of the joint replacement device in response to lateral forces exerted by the first member on the second member, and (ii) the apparatus and method include a third unit or step operable to impart rotational displacement to the first member of the joint replacement device such that the articulation surface of the first member will be engaged with the articulation surface of the second member for the desired articulation of the first and second members.

30 Claims, 11 Drawing Sheets

METHOD AND APPARATUS FOR TESTING A JOINT REPLACEMENT DEVICE

This application claims the benefit of provisional application Ser. No. 60/567,484, filed May 3, 2004.

BACKGROUND

The present invention relates generally to apparatus and method for testing a joint replacement device and pertains, more specifically, to testing the respective components of a joint replacement device in articulation relative to one another under a load.

Artificial or prosthetic devices for replacing defective joints in humans have been the subject of extensive research and development efforts for many years, particularly with regard to hip and knee joints, and more recently with spinal joints. In the design of such devices, it is advisable to subject the components of each new design to static and dynamic testing. Such testing is prudent in that it ensures that a particular design will not fail prematurely. Thus, a need exists within the medical equipment industry to assess the endurance properties of components of joint replacements.

While machines suitable for testing artificial or prosthetic hip and knee joints are known and are available to provide a variety of loading and articulation combinations, such machines have several shortcomings, including large size, significant cost (both of purchase and maintenance), and slow speed. Moreover, many joint testing devices have been developed specifically for use with hip and knee joints, and in that respect are unsuitable for use with the growing number of spinal implants. The need to retrofit or completely redesign such machines for use with spinal implants increases the cost and, in some cases, the size of the machines.

There are some devices that purport to address some of the above-described shortcomings. For example, Enduratec (Minnetonka, Minn.) manufactures at least one Spinal Disc Implant Wear Testing System, the respective capabilities and features of which are summarized at http://www.enduratec.com/testapp.cfm/tid/29 and http://www.enduratec.com/testapp.cfm/tid/27. While utilizing newer technologies to increase speed and minimize size, these devices are nevertheless costly and complicated in function for many uses.

Therefore, there is a need in the field for new approaches to provide a joint replacement device testing machine and method that efficiently effect articulation of replacement joint components under a load.

SUMMARY OF THE INVENTION

The present invention includes, among other aspects, a testing apparatus and method primarily for use in evaluating performance characteristics of a replacement joint, and more particularly for testing the respective components of a joint replacement device in articulation relative to one another under a load. Replacement joint devices suitable for being evaluated using the techniques of the present invention include, for example, artificial hip joints, artificial knee joints, and intervertebral disc joints.

In accordance with one or more aspects of the present invention, an apparatus and method for testing components of a joint replacement device in articulation relative to one another under a load include a first step performed by a first unit operable to impart undulating orientations of a first member of the joint replacement device; and a second step performed by a second unit operable to locate a second member of the joint replacement device proximate to the first member of the joint replacement device such that an articulation surface of the second member engages an articulation surface of the first member for articulation in response to the undulating orientations of the first member.

The first unit preferably includes: (i) a base operable for rotational movement about a first longitudinal axis and including a slanted plane with respect to a first plane substantially perpendicular to the first longitudinal axis, and (ii) an undulating platform rotationally coupled to the base about a second longitudinal axis and oriented in a second plane that is substantially perpendicular to the second longitudinal axis and that is substantially parallel to the slanted plane of the base. Thus, the rotational movement of the base about the first longitudinal axis causes undulating orientations of the slanted plane and corresponding undulating orientations of the undulating platform by way of its rotational coupling to the base. As the first member of the joint replacement device is coupled to the undulating platform, it likewise undulates.

While the base is operable to rotate through one or more 360 degree cycles about the first longitudinal axis, the undulating platform is restricted in its ability to rotate and does not rotate through a full 360 degree cycle about the first longitudinal axis. This may be achieved by providing a longitudinal race in substantially parallel orientation with respect to the first longitudinal axis, and an arm extending from the undulating platform into the longitudinal race such that the undulating platform is restricted in its ability to rotate about the first longitudinal axis. The arm is operable to move longitudinally within the longitudinal race in response to the undulating orientations of the undulating platform.

In order to achieve a desired rotational displacement of the undulating platform, the longitudinal race is operable to move substantially tangentially with respect to the first longitudinal axis to impart rotation to the first member of the joint replacement device about the first longitudinal axis such that the articulation surface of the first member rotationally engages the articulation surface of the second member. Preferably, the longitudinal race is operable to oscillate between first and second extremes in order to limit the rotation of the first member of the joint replacement device about the first longitudinal axis.

The apparatus may further include an offset crank and a rocker arm coupled between the crank and the longitudinal race to move the longitudinal race substantially tangentially with respect to the first longitudinal axis. Preferably, at least one of: (i) a frequency of oscillation between the first and second extremes is selectively variable; and (ii) the positions of the first and second extremes are selectively variable.

Preferably the second unit is operable to automatically adjust the location of the second member of the joint replacement device in response to lateral forces exerted by the first member upon the second member during the undulating orientations. To this end, the second unit may include a shaft having a proximal end for operative connection to the second member of the joint replacement device, and a hinge unit operable to maintain the shaft in substantially coaxial orientation with respect to a first longitudinal axis passing through the central portion of the articulation surface of the first member of the joint replacement device.

The hinge unit permits the lateral movement of the first member to move the second member of the joint replacement device such that the shaft is maintained in substantially coaxial orientation with respect to the first longitudinal axis.

For example, the hinge unit may include: a first pivot assembly operable to permit the shaft to rotate about a second longitudinal axis oriented substantially parallel to the shaft; and a second pivot assembly operable to permit the shaft and the first pivot assembly to rotate about a third longitudinal axis oriented substantially parallel to the shaft.

Preferably, the apparatus and method include the capability of loading the first and second members of the joint replacement device in compression. To this end, the method and apparatus may further include: a further step carried out by a load unit operable to impart a load on the shaft such that the articulation surfaces of the first and second members of the joint replacement device are in compression. Preferably, the load unit is operable to control the load on the shaft to achieve a substantially constant compressive load as between the articulation surfaces of the first and second members of the joint replacement device. For example, the load unit may include: a drive shaft, preferably in the form of a screw shaft, in alignment with, and coupled to, the shaft; and an actuator, preferably in the form of a motor, coupled to and operable to bias the drive shaft towards the shaft, preferably by rotating the screw shaft within a threaded coupling such that the threaded coupling biases the screw shaft towards the shaft and imparts the load on the shaft. The motor is preferably a servo motor that is controlled to variably rotate the screw shaft to achieve a substantially constant compressive load as between the articulation surfaces of the first and second members of the joint replacement device.

Other aspects, features, and advantages of the present invention will be apparent to one skilled in the art from the description herein taken in conjunction with the accompanying drawings.

BRIEF DESCRIPTION OF THE DRAWINGS

For the purposes of illustration, there are shown in the drawings forms that are presently preferred, it being understood, however, that the invention is not limited to the precise arrangements and instrumentalities shown.

DETAILED DESCRIPTION OF THE PREFERRED EMBODIMENTS

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

Figure 1:
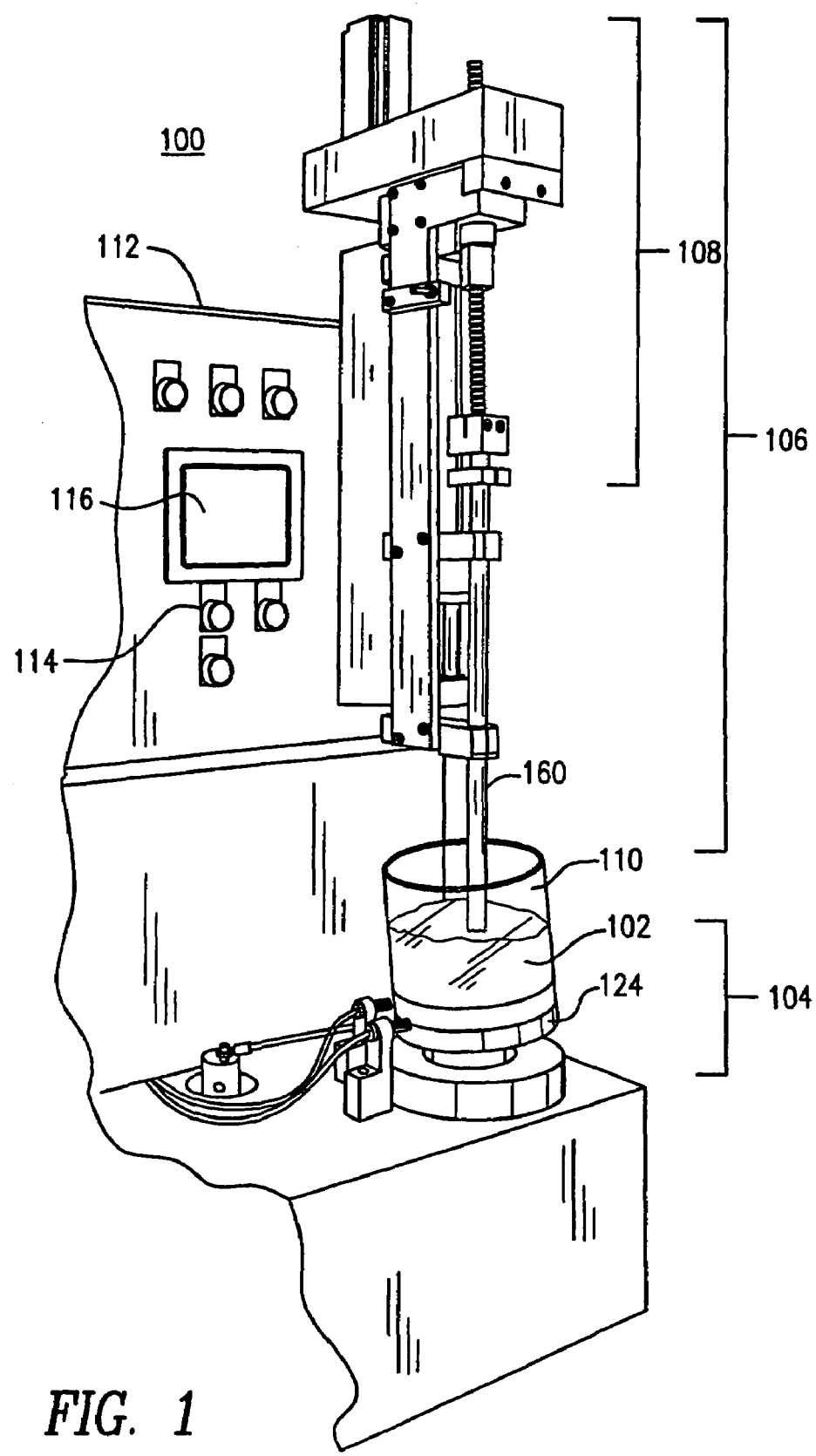
FIG. 1 is a perspective view of a testing apparatus operated in accordance with and embodying one or more aspects of the present invention.

With reference to FIG. 1, an embodiment of a testing apparatus 100 operated in accordance with one or more aspects of the present invention is illustrated. In general, the testing apparatus 100 is operable to articulate respective components of a joint replacement device with respect to one another under a load and over repeated cycles in order to evaluate performance and reliability of the joint replacement device. The testing apparatus 100 includes a first unit generally designated 104 and a second unit generally designated 106 that are operable to locate the respective components of the joint replacement device in proximity to one another such that they may be articulated against one another in a way that mimics the movement that would be experienced within the human body. For example, the joint replacement device may be an intervertebral disk replacement device for a human spinal column and the first and second units 104, 106 of the testing apparatus 100 may be operable to articulate respective components of the intervertebral disk replacement device with respect to one another to mimic the movement that the joint replacement device would experience within the spinal column.

Figure 2:
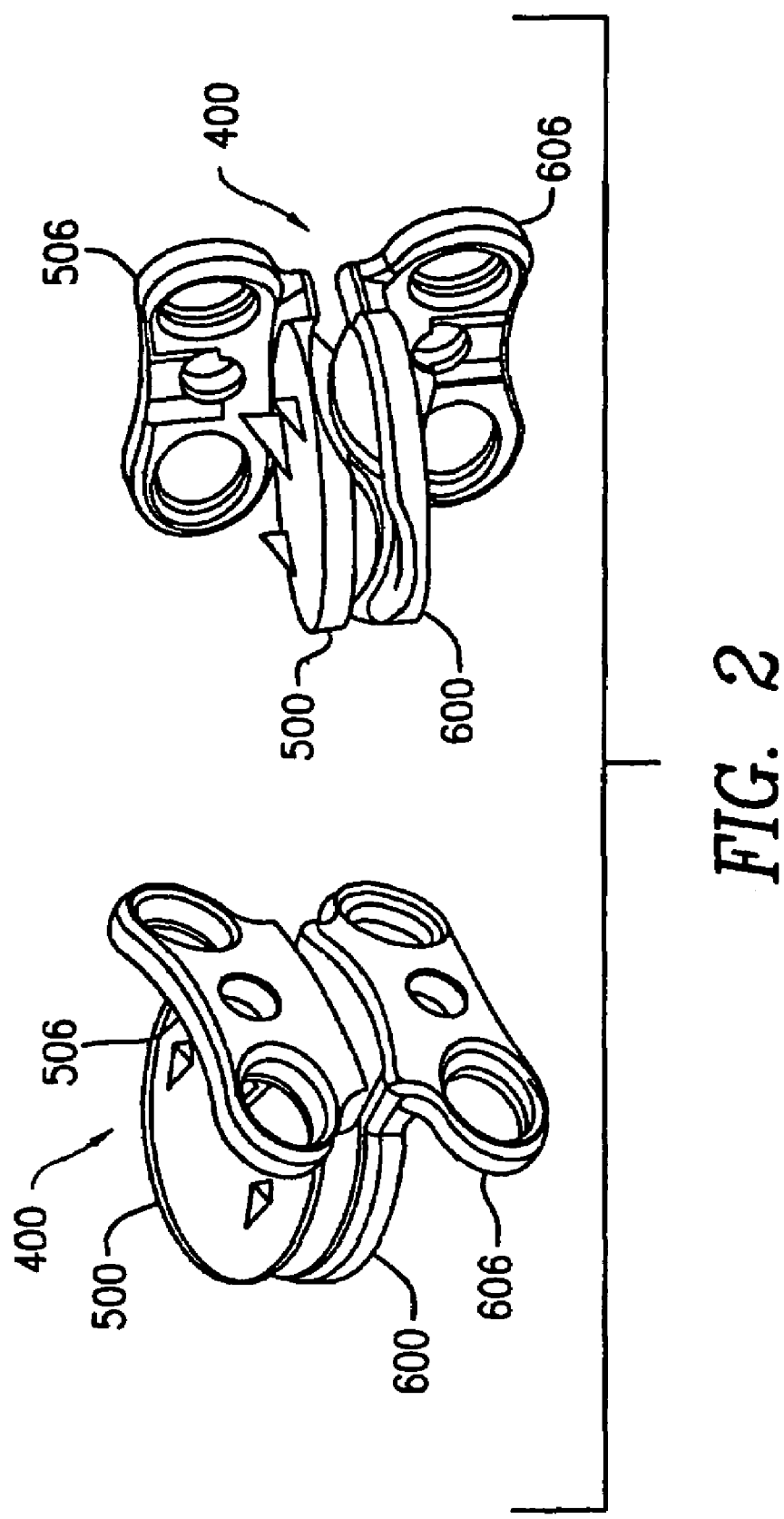
FIG. 2 includes perspective views of a joint replacement device that may be subject to tests by the method and apparatus of FIG. 1.

As shown in FIG. 1, the preferred components of the joint replacement device are submerged within a liquid 102 and thus are best seen in FIG. 2. The joint replacement device, for example, may be an intervertebral disk replacement device 400, which includes first and second members, shown in the form of an upper element 500, comprising the second member, and a lower element 600, comprising the first member, which members are operable to articulate against one another by way of respective saddle-shaped articulation surfaces. The intervertebral disk replacement device 400 is particularly suited for replacing an intervertebral disk in a spinal column, such as the cervical spine. Respective flanges 506, 606 of the upper and lower elements, 500, 600 may be used to fix the device 400 to respective vertebral bones of the spinal column such that the upper and lower elements 500, 600 are disposed within the intervertebral space between the vertebral bones. Further details concerning the intervertebral disk replacement device 400 may be found in co-pending U.S. patent application Ser. No. 10/688,632, entitled Instrumentation And Methods For Use In Implanting A Cervical Disk Replacement Device, filed Oct. 17, 2003, now published under Publication No. 2004-0176776, dated Sep. 9, 2004, and Ser. No. 10/382,702, entitled Cervical Disk Replacement, filed Mar. 6, 2003, now published under Publication No. 2004-0176844, dated Sep. 9, 2004, the entire disclosures of which are hereby incorporated by reference. The remainder of this specification will refer to the joint replacement device 400 illustrated in FIG. 2 in connection with describing the testing apparatus 100. It should be noted, however, that the reference to the specific design of the joint testing apparatus 400 is for illustration only and that various aspects of the present invention may be used in connection with testing other designs and configurations.

Referring again to FIG. 1, the lower element 600 of the device 400 is coupled to the first unit 104 such that the first unit 104 is operable to impart undulating orientations to the lower element 600. The upper element 500 is preferably coupled to the second unit 106 of the testing apparatus 100 such that the upper element 500 is located proximate to the lower element 600 and the respective articulation surfaces of the elements 500, 600 movingly engage one another in response to the undulating orientations of the lower element 600.

The first unit 104 generally includes an undulating platform 124 to which the lower element 600 of the joint replacement device 400 is coupled. The second unit 106 includes a shaft 160 having a proximal end (within the liquid 102 as illustrated) for operative connection to the upper element 500 of the joint replacement device 400. The shaft 160 remains relatively stationary as compared with the undulating platform 124 in order to achieve the sliding engagement of the respective articulation surfaces of the joint replacement device 400. Further, the second unit 106 of the testing apparatus 100 includes a load unit 108 that is operable to impart a load on the shaft 160 such that the articulation surfaces of the joint replacement device 400 are in compression. The testing apparatus 100 is operable to cycle the joint replacement device 400 through numerous articulation cycles under a compressive load in order to mimic the environmental conditions to which the joint replacement device 400 would be subject within the human body.

The testing apparatus 100 also preferably includes a controller 112 that is operable to automatically control various aspects of the apparatus 100. For example, the controller 112 is preferably operable to receive set-up commands from an operator through one or more input switches 114 and/or a touch sensitive display screen 116. A preferred set of such set-up commands will be discussed later in this description. Further, the controller 112 is preferably operable to control the electromechanical functions of the apparatus 100 by way of executing suitable software instructions (in light of the set-up commands) and receiving various feedback data from certain sensors located at key points within the apparatus 100. As will become more apparent from the description hereinbelow, the controller 112 may be implemented utilizing suitable hardware of known technologies, such as standard digital circuitry, analog circuitry, any of the known processors that are operable to execute software and/or firmware programs, one or more programmable digital devices or systems, such as programmable read only memories (PROMs), programmable array logic devices (PALs), any combination of the above, and the like.

For some uses of the testing apparatus 100 of the present invention, it may be desirable to submerge the joint replacement device 400 in the liquid 102 so that any wear debris generated as a result of the articulation of the components of the joint replacement device during the testing procedure can be captured and later analyzed. In the embodiment of the testing apparatus 100 of the present invention illustrated in FIG. 1, a cylindrical tank 110 is mounted on the undulating platform 124 and includes a surface (not shown) that is substantially parallel to the general planar orientation of the undulating platform 124. The lower element 600 of the joint replacement device 400 is coupled to the surface of the cylindrical tank 110 such that the sides of the tank 110 surround the upper and lower elements 500, 600 of the joint replacement device 400 to a height sufficient to submerge the device 400 during articulation cycles. It is noted that other tank designs or other structures, shapes, sizes and/or configurations can alternatively or additionally be used to achieve such submersion of the device 400 without departing from the scope of the present invention. It should be noted that, while a submersion tank 110 is preferred, it is not required to practice all aspects of the present invention.

Figure 3:
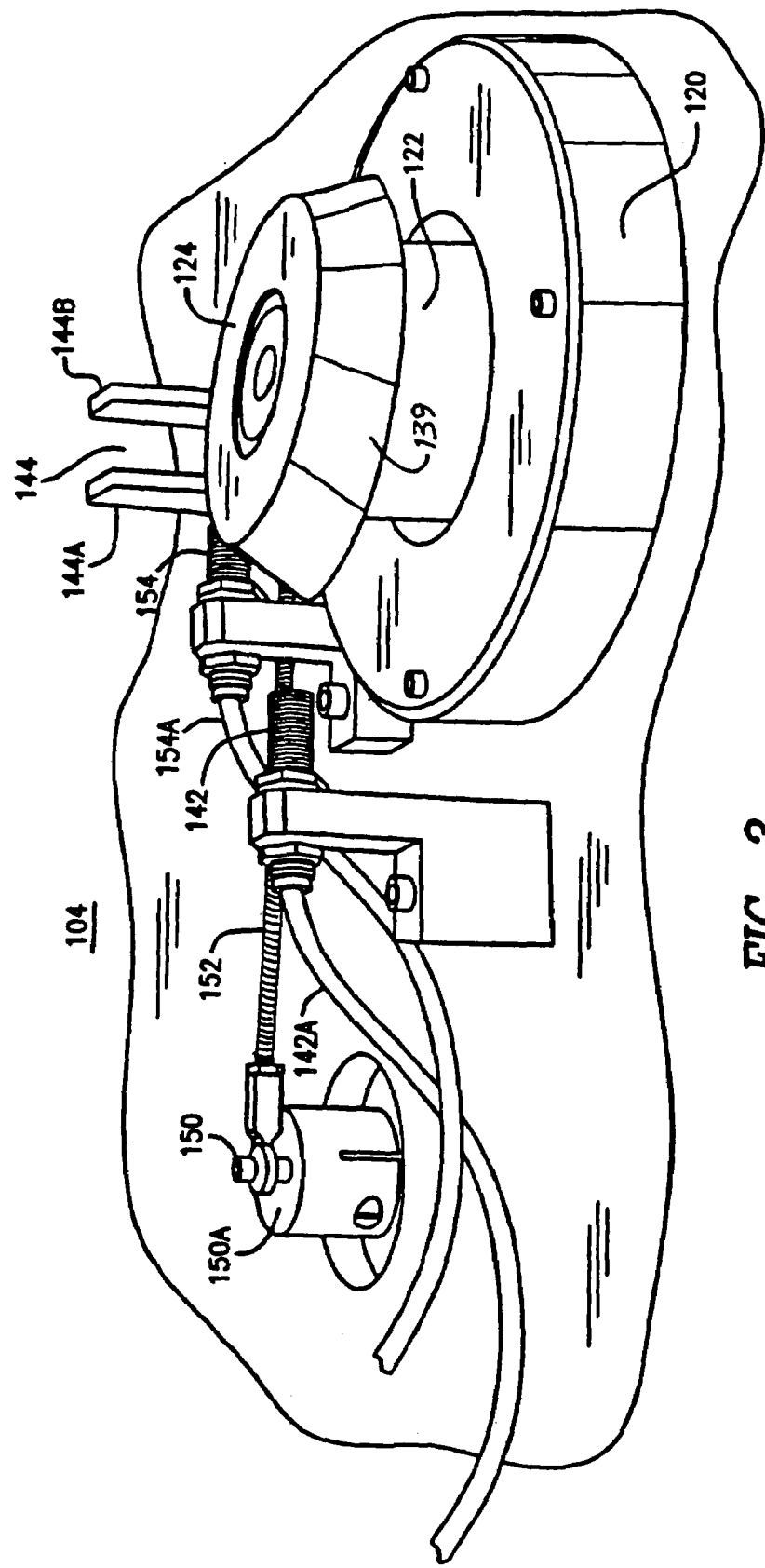
FIG. 3 is a perspective view of a portion of the testing apparatus of FIG. 1.
Figure 4:
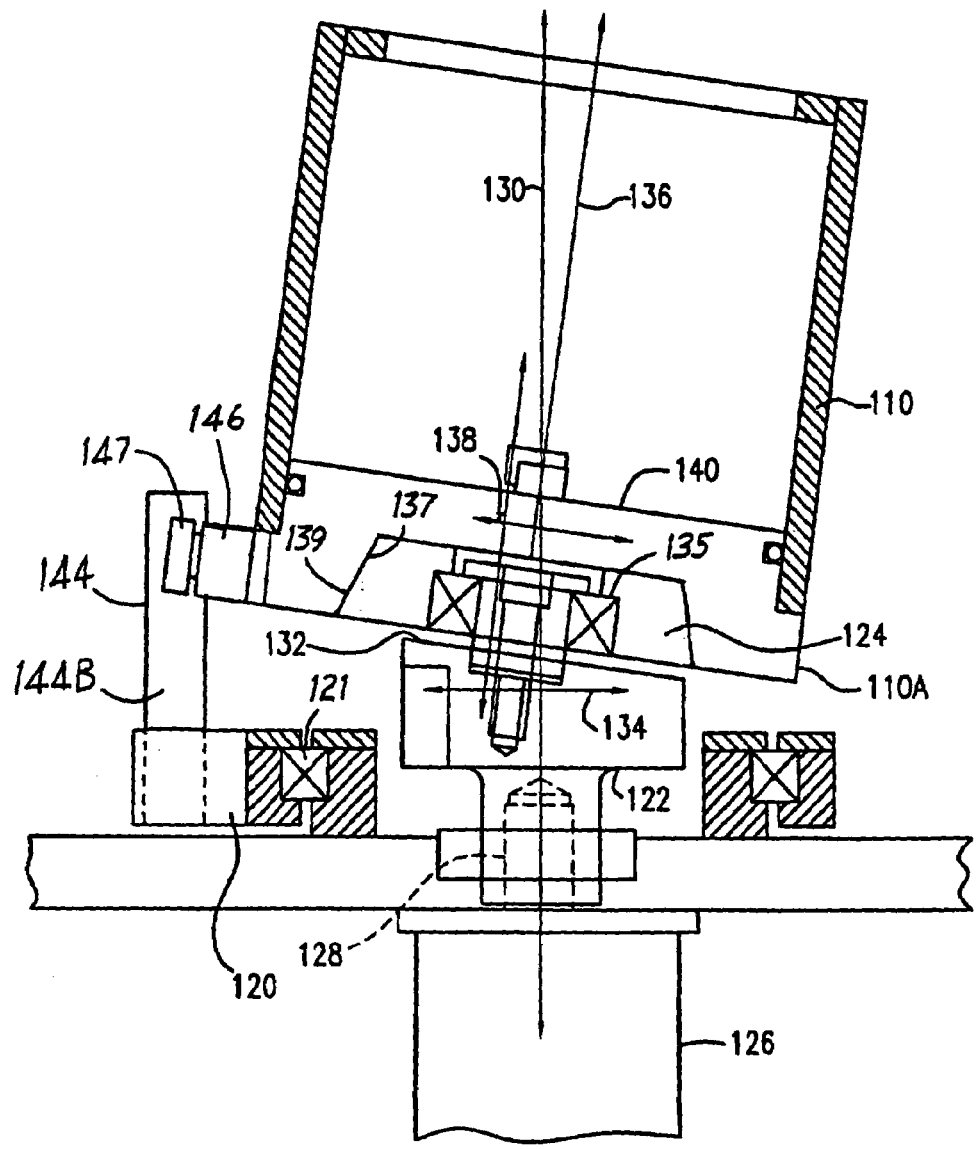
FIG. 4 is a largely schematic side view of one or more parts of the portion of the testing apparatus of FIG. 3.

Reference is now made to FIGS. 3 and 4, which illustrate an embodiment of the first unit 104 of the testing apparatus 100. The first unit 104 includes an annular platform 120, a rotating base 122, an undulating platform 124, and an undulating motor 126. The undulating motor 126 is fixed to a stationary frame of the testing apparatus 100 and includes a shaft 128 that is coupled to the rotating base 122 in order to impart rotational torque thereto. In operation, the undulating motor 126 is preferably operable to rotate the rotating base 122 at a desired frequency, such as 1.5 Hz, it being understood that various aspects of the invention permit variability in this frequency by way of user-specified inputs to the controller 112. The rotating base 122 rotates about a first longitudinal axis 130 and includes a slanted plane represented by surface 132 which is shown slanted with respect to a first plane 134. The first plane 134 is substantially perpendicular to the first longitudinal axis 130. Thus, when the motor 126 rotates the base 122, the slanted surface 132 rotates and undulates with reference to a stationary vantage point.

The undulating platform 124 is rotationally coupled to the base 122 by way of any of the known or hereinafter developed bearings, one of which is illustrated as bearing 135. The undulating platform 124 rotates about a second longitudinal axis 136 and is oriented in a second plane 138 that is substantially perpendicular to the second longitudinal axis 136. The undulating platform 124 also includes an upper surface 140 that is substantially parallel to the second plane 138 and the slanted surface 132 of the rotating base 122. The rotational movement of the rotating base 122 about the first longitudinal axis 130 causes undulating orientations of the upper surface 140 of the undulating platform 124 by way of the rotational coupling of the undulating platform 124 to the base 122.

Although the base 122 is preferably permitted to rotate through 360° cycles about the first longitudinal axis 130, the undulating platform 124 is preferably restricted in its ability to rotate about the first longitudinal axis 130. While the particular mechanism by which the rotation of the undulating platform 124 is restricted will be discussed later in this description, the consequence of such restriction in combination with the rotational coupling between the rotating base 122 and the undulating platform 124 is that undulating orientations of the upper surface 140 of the undulating platform 124 are obtained without rotation of the undulating platform 124 about the first longitudinal axis 130. As will be discussed in more detail hereinbelow, restricted or partial rotations of the undulating platform 124 about the first longitudinal axis 130 may be permitted but they are preferably not substantial rotational displacement as compared to the 360° rotational cycling of the rotating base 122. Thus, assuming substantially no rotational displacement of the undulating platform 124 about the first longitudinal axis 130, the rotational movement of the base 122 about the first longitudinal axis 130 will cause orientations of the second longitudinal axis 136 (which is normal to the upper surface 140) of the undulating platform 124 to sweep through a frustoconical path. In this sense, the undulating platform 124, and the upper surface 140 thereof in particular, achieve undulating orientations with respect to a stationary vantage point. As the lower element 600 of the joint replacement device 400 is preferably coupled directly or indirectly to the upper surface 140 of the undulating platform 124, the articulation surface of the lower element 600 also achieves undulating orientations.

In a preferred embodiment of the invention, the undulating platform 124 is rotationally coupled to the rotating base 122 such that: (i) the first longitudinal axis 130 passes through a center of rotation of the slanted surface 132 of the base 122, and (ii) the second longitudinal axis 136 passes through a center of rotation of the articulation surface of the lower element 600 of the joint replacement device 400 and through a point on the slanted surface 132 of the base 122 that is offset from the center of rotation of the slanted surface 132. One skilled in the art will appreciate that this configuration results in minimized translational offsets of the lower element 600 with respect to the first longitudinal axis 130. Indeed, if the undulating platform 124 were coupled to the rotating base 122 such that the second longitudinal axis 136 (which passes through the center of rotation of the undulating platform 124) were to also pass through the center of rotation of the slanted surface 132, then the lower element 600 of the joint replacement device 400 would sweep through a circular path at a radius away from the first longitudinal axis 130. For reasons that will become more apparent below, it is desirable to minimize any translational movement of the lower element 600 of the joint replacement device 400 away from the first longitudinal axis 130 during the undulating orientations of the undulating platform 124.

For the purposes of testing the joint replacement device 400 shown in FIG. 2, it has been found that an angle of about 6° to 7° in defining the slanted surface 132 of the rotating base 122 is satisfactory. It is understood, however, that other angles of inclination may be utilized for testing other joint replacement devices with differing characteristics without departing from the spirit and scope of the present invention. It is also noted that while a slanted surface 132 of the rotating base 122 is preferred, other configurations are contemplated as being within the scope of the present invention. For example, the rotating base 122 need not employ a slanted surface 132 that extends over the entire upper portion thereof. Instead, a smaller slanted surface standing off from the rotating base 122 may be employed to facilitate the rotational coupling to the undulating platform 124 to achieve the desired angulation between the first longitudinal axis 130 and the second longitudinal axis 136. Still further, the rotating base 122 may employ any other mechanism that facilitates the rotational coupling of the undulating platform 124 at the desired angle that does not require a slanted surface 132. For example, the rotating base 122 may include a bore at the desired angle that receives a coupling post from the undulating platform 124 to facilitate the rotational coupling thereof at the desired angulation. Alternatively, the rotating base 122 may include a coupling post extending therefrom at the desired angle, which is received by the undulating platform 124 in order to achieve the rotational coupling. Irrespective of the particular mechanism employed, the desirable result is that the base 122 rotates about the first longitudinal axis 130, while the undulating platform 124 is coupled to the rotating base 122 for rotation about a second longitudinal axis 136 that is at a desired angle to the first longitudinal axis 130.

With reference to FIGS. 5–8, further details concerning the undulating orientations of the undulating platform 124 and the cylindrical tank 110 may be understood. As illustrated in these figures, the cylindrical tank 110 is mounted to the undulating platform 124 by way of a lower plate 110A having a tapered recess 137 engaged with a complementary tapered rim 139 on the platform 124 to secure the lower plate 110A to the platform 124 for movement of the lower plate 110A with the platform 124. As discussed above, the lower element 600 of the joint replacement device 400 is submerged within the liquid 102 and coupled to the undulating platform 124 through the lower plate 110A. It is noted, that intermediate coupling elements may be disposed between the lower element 600 of the joint replacement device 400 and the lower plate 110A without departing from the spirit and scope of the present invention. Indeed, irrespective of the extent of intermediate coupling elements, the preferable result is that the general planar orientation of the lower element 600 of the joint replacement device 400 is substantially parallel to the second plane 138 of the undulating platform 124.

Figure 5:
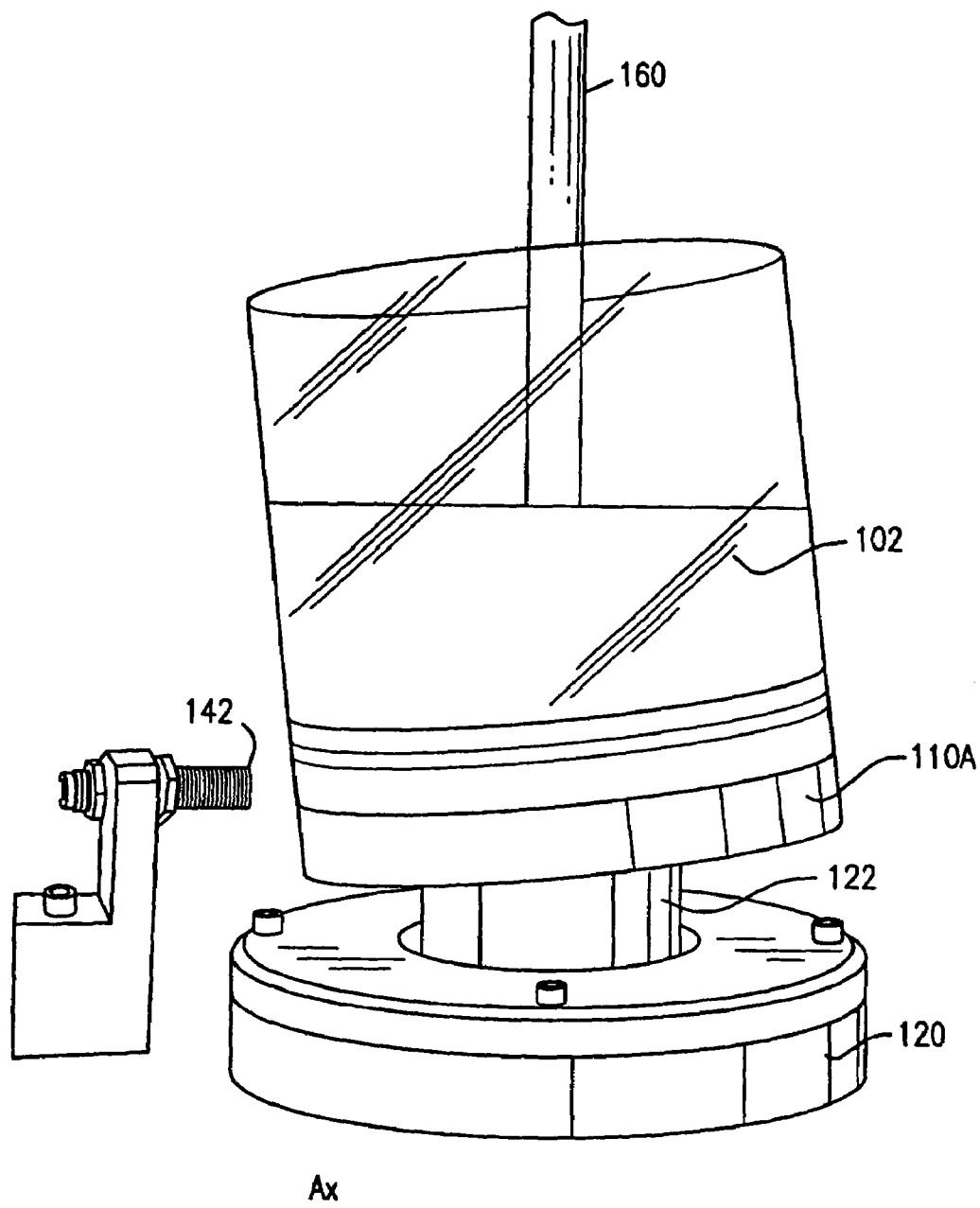
FIG. 5 is a front view of an undulating portion of the test apparatus in a first orientation.
Figure 6:
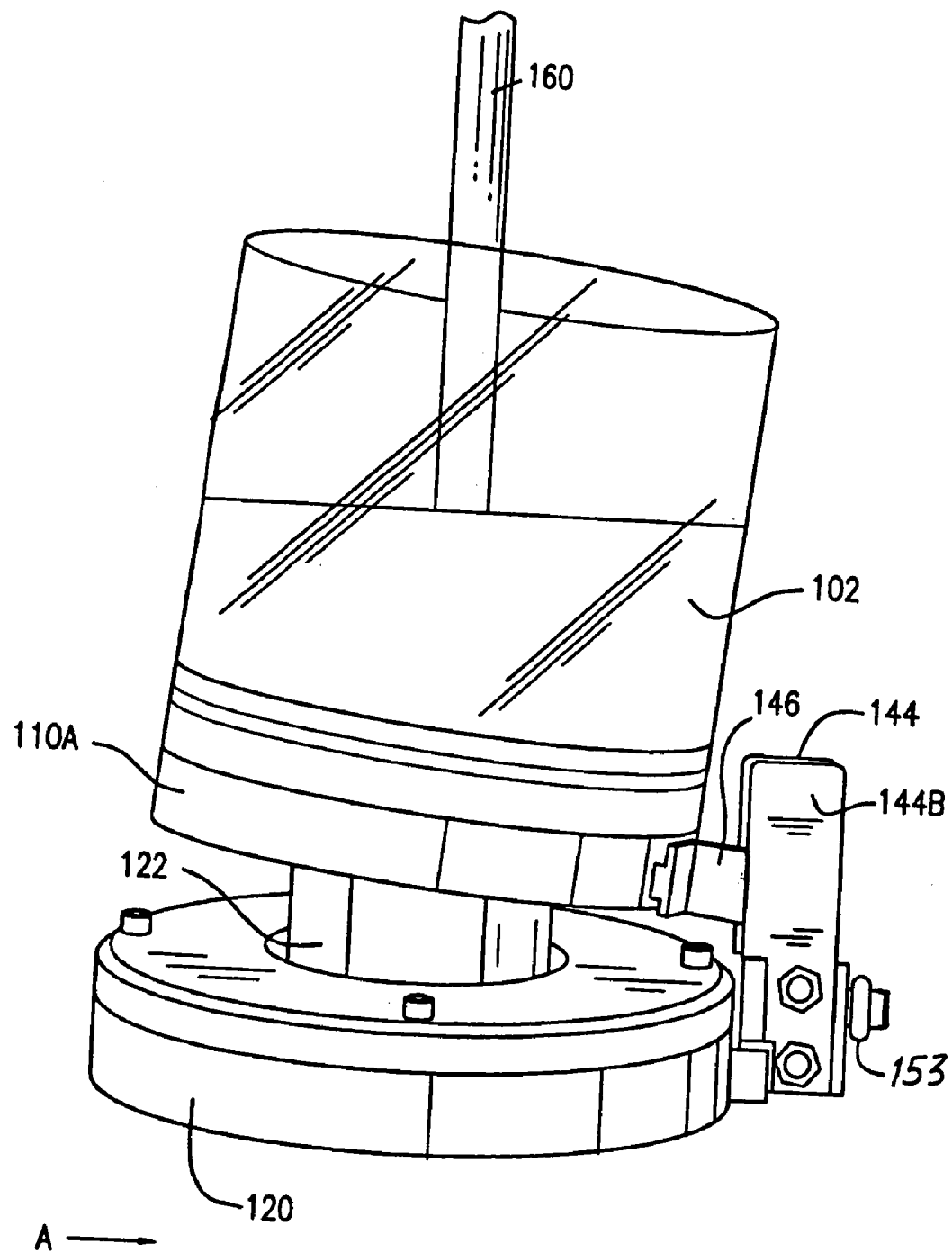
FIG. 6 is a side view of the undulating portion of the test apparatus in a second orientation.
Figure 7:
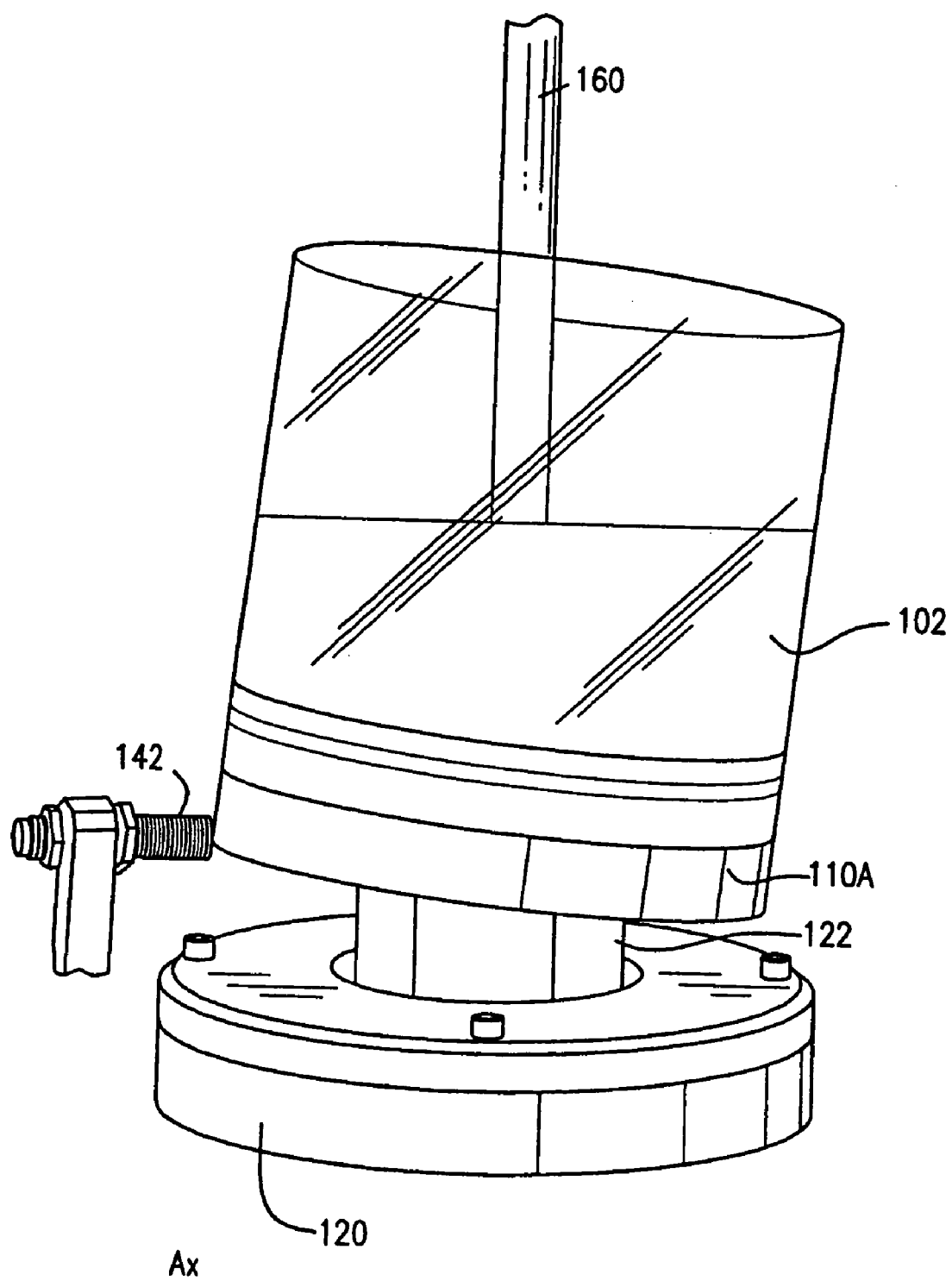
FIG. 7 is a front view of the undulating portion of the test apparatus in a third orientation.

As illustrated in FIG. 5, the undulating platform 124 is in an orientation in which the normal vector to the upper surface 140 of the undulating platform 124 is in an upward and leftward direction when viewed from direction A. With reference to FIG. 6, when the rotating base 122 has rotated through 90° clockwise, the normal vector to the undulating platform 124 is in an upper and rearward direction when viewed from direction A. With reference to FIG. 7, when the rotating base 122 has rotated through another 90°, the normal vector to the undulating platform 124 is in an upper and rightward direction when viewed from direction A. Finally, with reference to FIG. 8, when the rotating base 122 has rotated through another 90°, the normal vector to the undulating platform 124 is in an upper and forward direction when viewed from direction A. It is to be understood that FIGS. 5–8 provide only four instances of the undulating orientations of the undulating platform 124 and that there are an infinite number of other orientations of the undulating platform 124 as the rotating base 122 continuously moves through one or more 360° cycles of rotation.

In general, the shaft 160 maintains the upper element 500 of the joint replacement device 400 in a substantially fixed orientation such that the undulating orientations of the platform 124 and the resulting orientations of the lower element 600 of the joint replacement device 400 cause articulation between the respective articulation surfaces of the joint replacement device 400 that may mimic the articulation that would be present in a human being, for example, in an intervertebral space of a spinal column.

Preferably, the frequency of rotation of the rotating base 122 about the first longitudinal axis 130 is controlled by the controller 112 and may be varied in response to user-defined criteria. In particular, the user may enter a desired frequency of rotation by way of the input switches 114 and/or the touch-sensitive screen 116. While a frequency of rotation of the rotating base 122 of 1.5 Hz is preferred, any other frequency of rotation is considered within the spirit and scope of the present invention. To facilitate the variable control of the frequency of rotation of the rotating base 122 about the first longitudinal axis 130 by the controller 112, the apparatus 100 may include a sensor 142 that is located proximate to one or more of the components of the first unit 104 in order to sense the rotational frequency of the rotating base 122 and provide a feedback signal (by way of wire 142A) to the controller 112. As best seen in FIGS. 3, 5 and 7, the sensor is preferably disposed proximate to the lower plate 110A of the tank 110 in order to sense the undulating movements thereof. While any of the known or hereinafter developed sensors may be utilized to implement sensor 142, it is preferred that sensor 142 is a proximity sensor of the magnetic type.

In response to the feedback signal from the sensor 142, the controller 112 may compare the feedback signal with a set-up command specifying a desired rotational frequency and modify the drive signaling to the undulating motor 126 to insure that the desired rotational frequency is achieved. This feedback configuration may also sense whether cycling has ceased for some reason (perhaps failure) and provide an indication to automatically stop the testing process or take some other appropriate action.

It is noted that the undulating motor 126 is preferably implemented utilizing a 3-phase machine that varies its rotational frequency in response to a variable magnitude 3-phase input voltage. The controller 112 preferably includes a suitable motor driver circuit that is operable to provide the desired 3-phase voltage (and current) to the undulating motor 126 in response to a command signal from the controller 112 indicative of the desired frequency of rotation. Any of the known or hereinafter developed motor driver circuits may be employed. Further, any of the known or hereinafter developed motors may be employed to implement the undulating motor 126.

As discussed above, the undulating platform 124 is restricted in its ability to rotate about the first longitudinal axis 130 despite that the rotating base 122 rotates through one or more 360° cycles about the first longitudinal axis 130. Thus, the rotational coupling between the undulating platform 124 and the rotating base 122 permits the platform 124, the lower plate 110A (if utilized), any intermediate coupling elements, and the lower element 600 of the joint replacement device 400 achieve undulating orientations without rotation about the first longitudinal axis 130.

Figure 8:
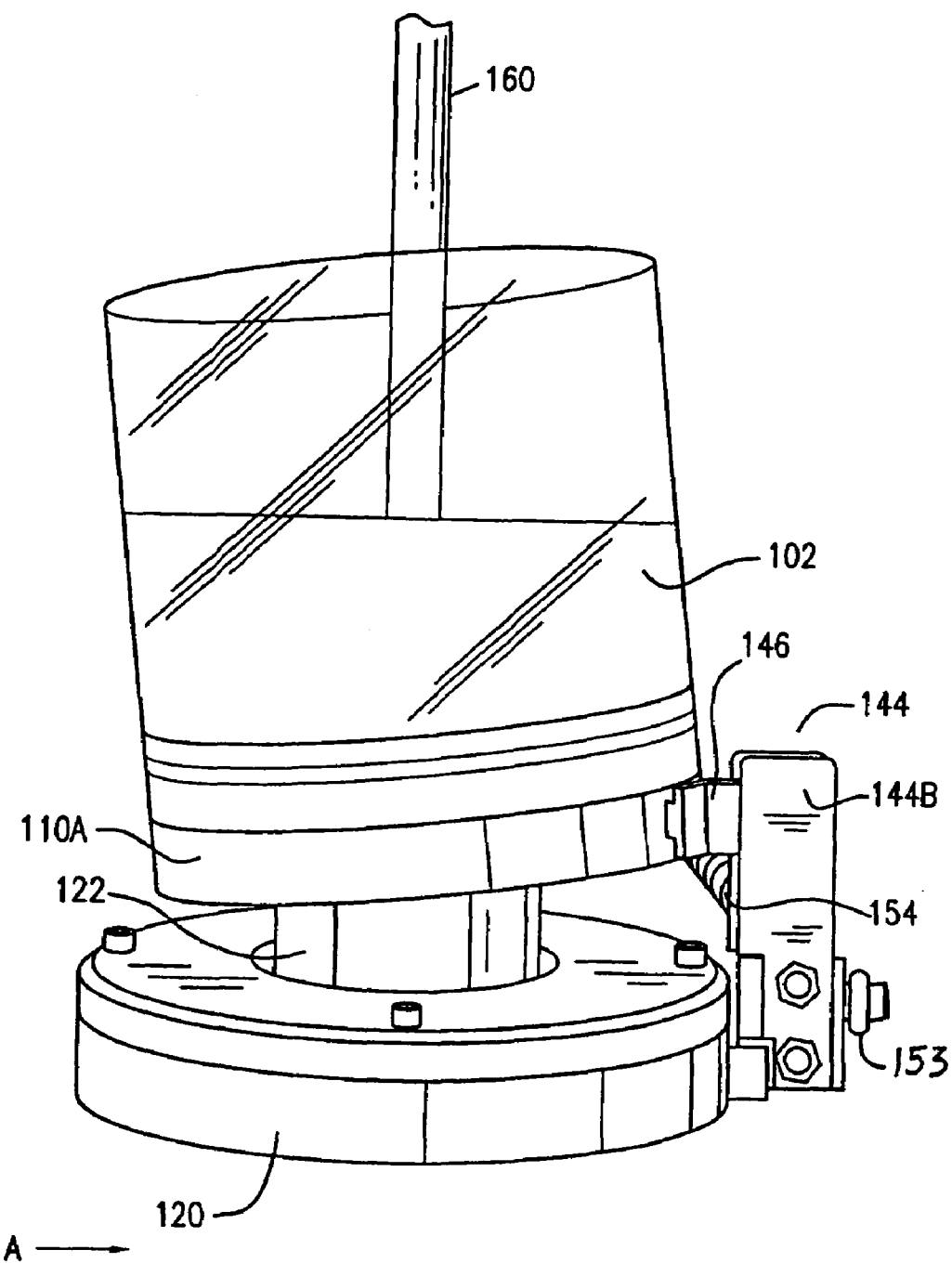
FIG. 8 is a side view of the undulating portion of the test apparatus in a fourth orientation.
Figure 9:
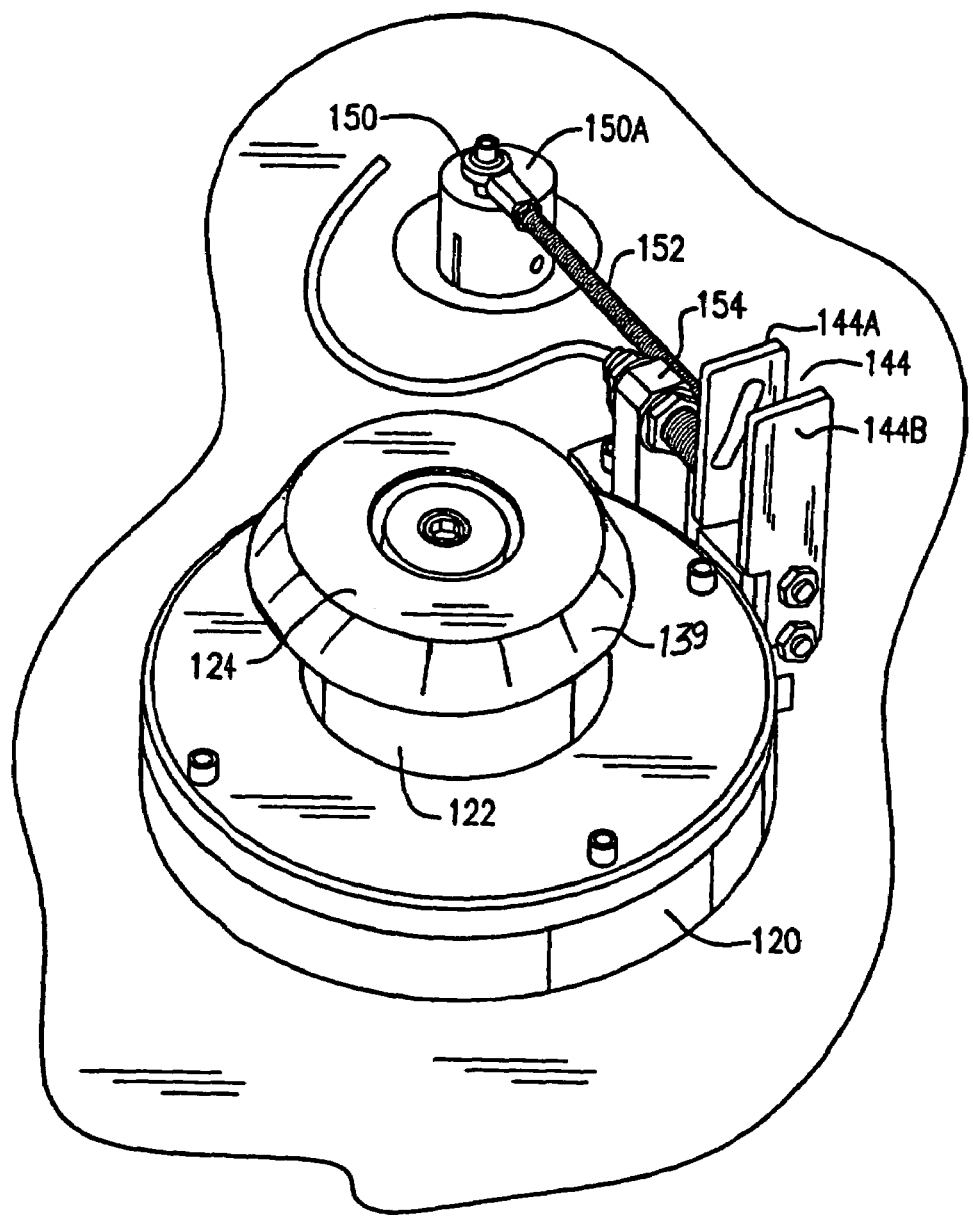
FIG. 9 is a further perspective view of the undulating portion of the test apparatus of FIG. 3.

As best seen in FIGS. 3, 8, and 9, the undulating platform 124 is preferably limited in its rotational displacement about the first longitudinal axis 130 by way of a longitudinal race 144 that is in a substantially parallel orientation with respect to the first longitudinal axis 130. The longitudinal race 144 may be implemented utilizing any of the known or hereinafter developed techniques, although it is preferred that the race 144 includes two substantially parallel plates 144A, 144B that are sized and shaped to receive an arm 146 extending from the undulating platform 124. The transverse orientation of the arm 146 within the longitudinal race 144 limits the rotation of the undulating platform 124 about the first longitudinal axis 130. It is noted that the arm 146 may extend (e.g., directly) from the undulating platform 124 when the tank 110 is not in use. Alternately, the arm 146 may extend (e.g., indirectly) from the undulating platform 124 when the tank 110 is in use by way of the lower plate 110A. In this sense, the undulating platform 124, the lower plate 110A of the cylindrical tank 110 (if utilized), and any intermediate coupling elements for connection to the lower element 600 of the joint replacement device 400 may be considered as part of the undulating platform 124 because they all cooperate to achieve undulating orientations with respect to the first longitudinal axis 130.

As best seen in FIGS. 6 and 8, the arm 146 cycles in a vertical motion pattern as the rotating base 122 rotates and the undulating platform 124 moves. In a preferred embodiment, the arm 146 includes a bearing 147 (see FIG. 4) that rides within the channel formed by the plates 144A, 144B to reduce friction as between the arm 146 and the race 144. Any of the known or hereinafter developed bearings or other devices may be utilized to reduce the frictional forces between the arm 146 and the longitudinal race 144.

Although the longitudinal race 144 and the arm 146 are operable to restrict the rotational displacement of the undulating platform 124 about the longitudinal axis 130, the restriction is preferably not absolute and some rotational displacement is preferably permitted when desired. Indeed, with reference to FIG. 2, the joint replacement device 400 may experience rotation as between the upper element 500 and the lower element 600 when implanted within, for example, a spinal column. Thus, in order to test such articulation (particularly under a load) the undulating platform 124 is preferably operable to rotate about the first longitudinal axis 130 in a controlled manner. For example, the undulating platform 124 is preferably operable to rotate about the first longitudinal axis 130 in a cyclical manner, but without rotating a full 360°. More particularly, the undulating platform 124 is preferably operable to rotate clockwise about the first longitudinal axis 130 through some limited angle of rotational displacement and then cycle back in a counter-clockwise direction through another limited angle. As to the joint replacement device 400, rotations of about ±3° are desirable and, therefore, the undulating platform 124 is preferably operable to rotate about the first longitudinal axis 130 in a cyclical fashion while limiting such rotation to about ±3° of rotational displacement.

Any of the known or hereinafter developed techniques may be utilized to implement the functionality of limited rotational movement of the undulating platform 124 about the first longitudinal axis 130. A preferred implementation is best illustrated in FIGS. 3 and 8 in which an offset crank 150, a rocker arm 152, and a linkage 153 (see FIGS. 6 and 8) cooperate to move the longitudinal race 144 somewhat tangentially with respect to the first longitudinal axis 130 to impart rotation to the lower plate 110A and thus to the undulating platform 124 and the lower element 600 of the joint replacement device 400. More particularly, the offset crank 150 includes a motor (not shown) that rotates a linkage 150A to which the offset crank 150 is connected. As the crank 150 is radially offset from the axis of the motor shaft, the rocker arm 152 (which is coupled to the offset crank 150) moves back and forth (left-to-right in FIG. 3) at a frequency corresponding to the rotational frequency of the motor. The linkage 153 (FIG. 8) couples the other end of the rocker arm 152 to the longitudinal race 144.

As best seen in FIG. 8, the longitudinal race 144 is connected to the annular platform 120 and the annular platform 120 is rotatable about the first longitudinal axis 130 without interfering with the rotational movement of the rotating base 122. Any of the known techniques for rotationally coupling the annular platform 120 to the stationary frame of the testing apparatus 100 may be employed, although it is preferred that an annular bearing 121 (see FIG. 4) is utilized in which a center race of the bearing 121 is fixed to the frame and an outer race of the bearing 121 is fixed to the annular platform 120. Irrespective of the particular rotational coupling mechanism employed, the cyclical movement of the rocker arm 152 translates such motion into rotational action of the undulating platform 124 about the first longitudinal axis 130 vis-a-vis the movement of the longitudinal race 144 against the arm 146.

Preferably, a frequency of undulation of the undulating platform 124 about the first longitudinal axis 130 is controlled by the controller 112 and may be varied in response to user-defined criteria. In particular, the user may enter a desired frequency by way of the input switches 114 and/or the touch-sensitive screen 116. While a frequency of the undulating platform 124 of 1.5 Hz is preferred, any other frequency is considered within the spirit and scope of the present invention. To facilitate the variable control of the frequency of the undulating platform 124 about the first longitudinal axis 130 by the controller 112, the apparatus 100 may include a sensor 154 that is located proximate to one or more of the components of the first unit 104 in order to sense the frequency of the undulating platform 124 and provide a feedback signal (by way of wire 154A) to the controller 112. While any of the known or hereinafter developed sensors may be utilized to implement sensor 154, it is preferred that sensor 154 is a proximity sensor of the magnetic type. In response to the feedback signal from the sensor 154, the controller 112 may compare the feedback signal with a set-up command specifying a desired frequency and modify the drive signaling to the motor to ensure that the desired frequency is achieved. This feedback configuration may also sense whether cycling has ceased for some reason (perhaps failure) and provide an indication to stop the testing process (perhaps automatically) or take some other appropriate action.

It is noted that the motor is preferably implemented utilizing a 3-phase machine that varies its rotational frequency in response to a variable magnitude 3-phase input voltage. The controller 112 preferably includes a suitable motor driver circuit that is operable to provide the desired 3-phase voltage (and current) to the motor in response to a command signal from the controller 112 indicative of the desired frequency of rotation. Any of the known or hereinafter developed motor driver circuits may be employed. Further, any of the known or hereinafter developed motors may be employed to implement the undulating motor 126.

Figure 10:
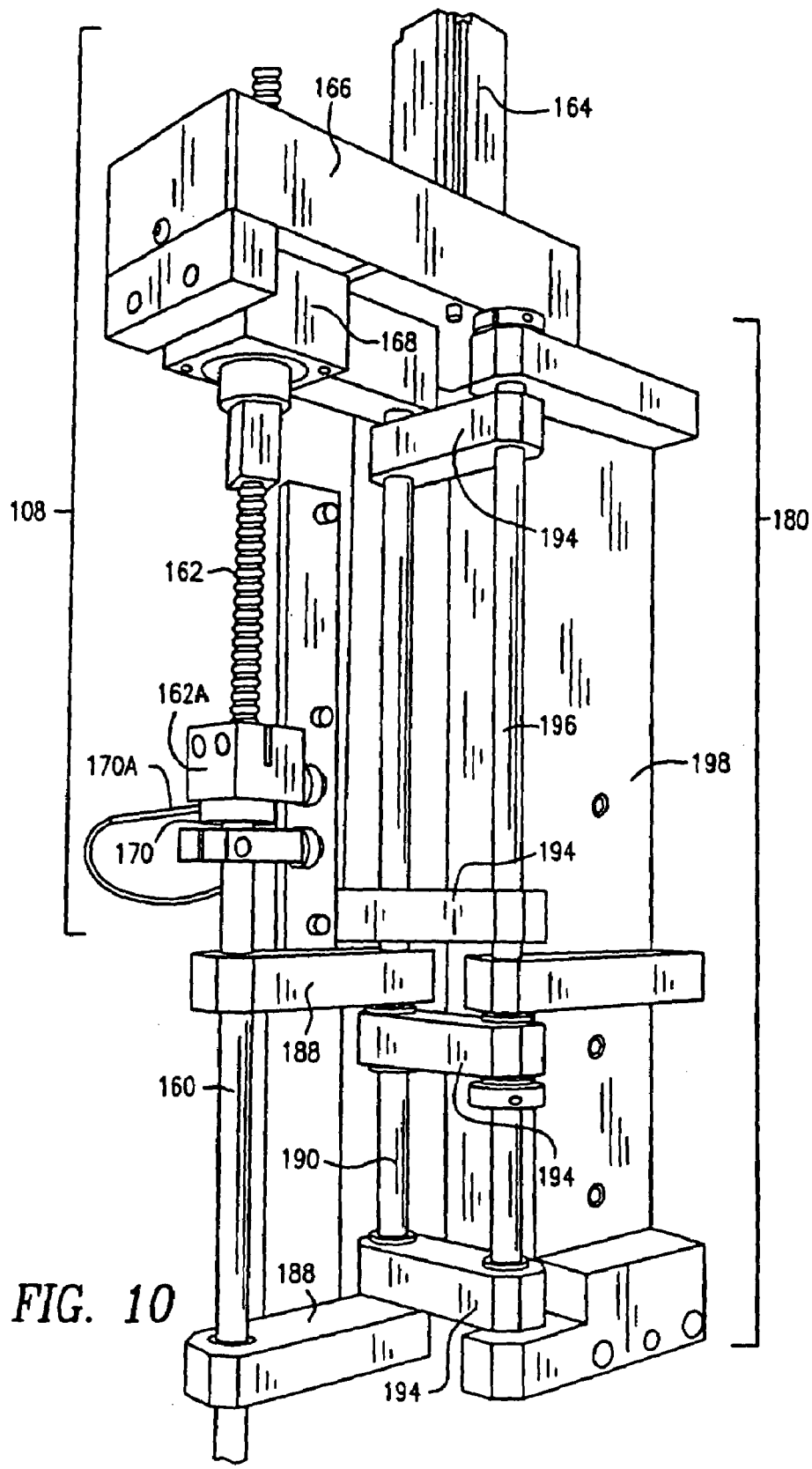
FIG. 10 is a perspective view of an upper portion of the testing apparatus of FIG. 1.
Figure 11:
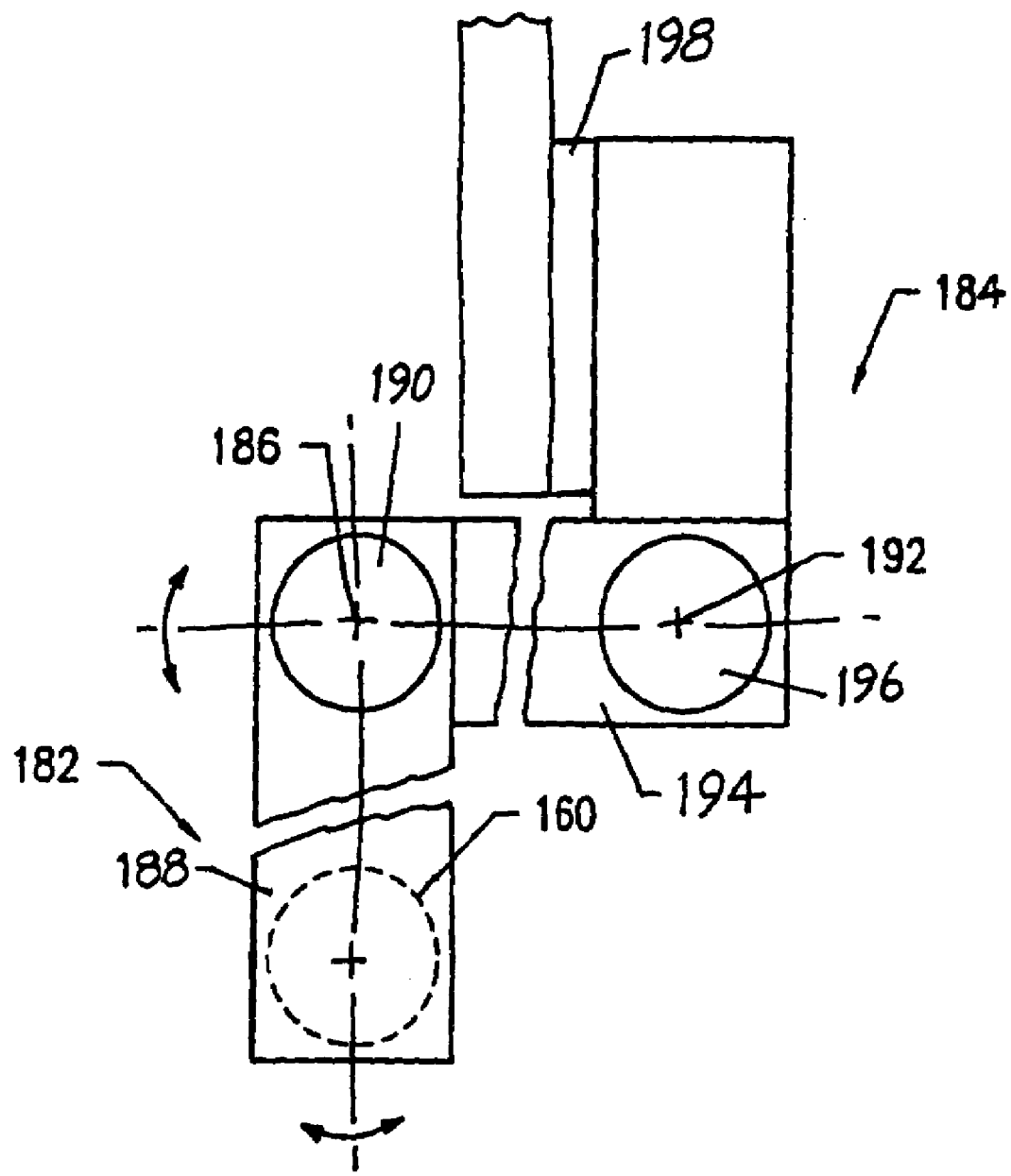
FIG. 11 is a top plan view of a portion of the upper portion of the testing apparatus of FIG. 10.

With reference to FIGS. 1, 10 and 11, the first unit 106 includes the load unit 108, the shaft 160, and a hinge unit 180 that are operable to position the shaft 160 (and the upper element 500) with respect to the lower element 600 of the joint replacement device 400 and to impart a load on the shaft 160 such that the upper and lower elements 500, 600 are in compression. Preferably, the load unit 108 is operable to impart a load on the shaft 160 in a controlled fashion to achieve a substantially constant compressive load as between the articulation surfaces of the first and second elements 500, 600 of the joint replacement device 400. In this regard, the load unit 108 includes a drive shaft, shown in the form of a screw shaft 162, an actuator, shown in the form of a load motor 164, and a drive unit 166. The screw shaft 162 is in alignment with, and is coupled to, the shaft 160 by way of a coupling unit 162A. The load motor 164 is coupled to the screw shaft 162 by way of the drive unit 166, which may include one or more suitable pulleys, belts, gears, chains, linkages and the like, such that the rotational torque produced by the load motor 164 may be transferred to the screw shaft 162. The load unit 108 further includes a threaded coupling 168 that is operatively engaged with the screw shaft 162 such that the screw shaft 162 is biased towards and/or away from the shaft 160 (and the lower element 600 of the joint replacement device 400) to control the load on the shaft 160 in response to rotational torques provided by the load motor 164.

Preferably, the load motor 164 is controlled by the controller 112 to maintain a substantially constant load in response to user-defined criteria. In particular, the user is preferably permitted to enter a desired load by way of the input switches 114 and/or the touch-sensitive screen 116. While a load of approximately 16 lbs. is preferred, any other load is considered within the spirit and scope of the present invention. It is noted, however, that if the shaft of the motor 126 (FIG. 4) is in direct alignment with the shaft 128 then some limits on the programmed load may be necessary. In order to achieve substantially higher loads than would be tolerable by the bearings of the motor 126, the motor 126 may be coupled to the rotating base 122 by way of an appropriate linkage that would transfer such load to intermediate bearings that could withstand substantial loading.

To facilitate the variable control of the load by the controller 112, the apparatus 100 may include a load sensor 170 that is located within the load unit 108 in order to sense the load on the shaft 160 and provide a feedback signal (by way of wire 170A) to the controller 112. In particular, the sensor 170 is preferably interposed between the screw shaft 162 and the shaft 160 in order to measure the actual load applied to the shaft 160. Any of the known or hereinafter developed sensors may be utilized to implement sensor 170. In response to the feedback signal from the sensor 170, the controller 112 may compare the feedback signal with a set-up command specifying the desired load and modify the drive signaling to the motor 164 to ensure that the desired load is achieved.

The load motor 164 is preferably implemented utilizing an appropriate servo motor that varies its rotational torque in one direction or the other in response to a variable magnitude input voltage. The controller 112 preferably includes a suitable motor driver circuit that is operable to provide the desired voltage (and current) to the load motor 164 in response to a command signal from the controller 112 indicative of the desired load. Any of the known or hereinafter developed motor driver circuits may be employed. Further, any of the known or hereinafter developed servo motors may be employed to implement the load motor 164.

The hinge unit 180 is preferably operable to maintain the shaft 160 in substantial alignment with respect to the first longitudinal axis 130 passing through a central portion of the articulation surface of the lower element 600 such that the upper element 500 and the lower element 600 are in desirable locations relative to one another for articulation. Preferably, the hinge unit 180 is operable to permit the shaft 160 and, consequently, the upper element 500 of the joint replacement device 400 to move in response to lateral forces applied by the lower element 600 when it achieves the undulating orientations, thereby automatically adjusting the location of the upper element 500 relative to the lower element 600 for the desired articulation.

With reference to FIGS. 10 and 11, the hinge unit 180 preferably includes a first pivot assembly 182 and a second pivot assembly 184. The first pivot assembly 182 is preferably operable to permit the shaft 160 (when viewed from above) to rotate about a longitudinal axis 186 that is oriented substantially parallel to the shaft 160. More particularly, the first pivot assembly 182 includes one or more lever arms 188 that are rotationally coupled to a shaft 190 that is coaxial with the longitudinal axis 186. (Alternately, the lever arms 188 could be fixed to the shaft 190 while the shaft 190 rotates to provide the desired movement of the shaft 160). The second pivot assembly 184 preferably is operable to permit the shaft 160 and the first pivot assembly 182 to rotate about a longitudinal axis 192 that is also oriented substantially parallel to the shaft 160. The second pivot assembly 184 preferably includes one or more lever arms 194 that are rotationally coupled to a shaft 196 that is coaxial with the longitudinal axis 192. (Alternately, the lever arms 194 could be fixed to the shaft 196 while the shaft 196 rotates).

Further, the shaft 196 is preferably fixed (at least translationally) to the frame 198 of the testing apparatus 100. The first and second pivot assemblies 182, 184 permit the shaft 160 to freely move in response to lateral forces exerted by the lower element 600 on the upper element 500 of the joint replacement device 400, thereby automatically adjusting the location of the upper element 500 relative to the lower element 600 for the desired articulation. Although the above-described configuration of the hinge assembly unit 180 is preferred, those skilled in the art will appreciate that numerous modifications thereof may be made without departing from the spirit and scope of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The embodiments of the invention in which an exclusive property or privilege is claimed are defined as follows:

1. An apparatus for testing components of a joint replacement device in desired articulation relative to one another under a load, comprising:
    a first unit operable to impart undulating orientations to a first member of the joint replacement device;
    the first unit including: (i) a base operable for rotational movement about a first longitudinal axis and having a slanted plane with respect to a first plane substantially perpendicular to the first longitudinal axis, and (ii) an undulating platform to which the first member of the joint replacement device is to be coupled, the undulating platform being rotationally coupled to the base about a second longitudinal axis and oriented in a second plane that is substantially perpendicular to the second longitudinal axis and that is substantially parallel to the slanted plane of the base such that rotational movement of the base about the first longitudinal axis causes the orientations of the second longitudinal axis of the undulating platform to sweep through a frusto-conical path and effects undulating orientations of the slanted plane and corresponding undulating orientations of the undulating platform by way of the rotational coupling between the undulating platform and the base; and
    a second unit operable to locate a second member of the joint replacement device proximate to the first member of the joint replacement device such that an articulation surface of the second member engages an articulation surface of the first member for articulation in response to the undulating orientations of the first member, the second unit being operable to automatically adjust the location of the second member of the joint replacement device relative to the first member for the desired articulation in response to lateral forces exerted by the first member upon the second member during the undulating orientations.

2. The apparatus of claim 1 wherein:
    the undulating platform is rotationally coupled to the base such that: (i) the first longitudinal axis passes through a center of rotation of the slanted plane of the base, and (ii) the second longitudinal axis passes through a center of rotation of the articulation surface of the second member of the joint replacement device and through a point in the slanted plane that is offset from the center of rotation of the slanted plane of the base; and
    the offset from the center of rotation of the slanted plane is such that the first longitudinal axis also substantially passes through the center of rotation of the articulation surface of the second member of the joint replacement device.

3. The apparatus of claim 1 wherein: the base is operable to rotate through one or more 360 degree cycles about the first longitudinal axis; and the undulating platform is restricted in its ability to rotate about the first longitudinal axis.

4. The apparatus of claim 3 wherein at least one of: (i) a frequency of rotation of the base about the first longitudinal axis is selectively variable; (ii) rotational displacement to which the undulating platform is restricted in its rotation about the first longitudinal axis is selectively variable; and (iii) a frequency of undulation of the undulating platform is selectively variable.

5. The apparatus of claims further comprising:
    a longitudinal race in substantially parallel orientation with respect to the first longitudinal axis; and
    an arm extending from the undulating platform into the longitudinal race such that the undulating platform is restricted in its ability to rotate about the first longitudinal axis.

6. The apparatus of claim 5 wherein the arm is operable to move longitudinally within the longitudinal race in response to the undulating orientations of the undulating platform.

7. The apparatus of claim 5 wherein the longitudinal race is operable to move substantially tangentially with respect to the first longitudinal axis to impart rotation to the first member of the joint replacement device about the first longitudinal axis such that the articulation surface of the first member rotationally engages the articulation surface of the second member.

8. The apparatus of claim 7 wherein the longitudinal race is operable to oscillate between first and second extremes in order to limit the rotation of the first member of the joint replacement device about the first longitudinal axis.

9. The apparatus of claim 8 further comprising an offset crank and a rocker arm coupled between the crank and the longitudinal race to move the longitudinal race substantially tangentially with respect to the first longitudinal axis.

10. The apparatus of claim 8 wherein at least one of: (i) a frequency of oscillation between the first and second extremes is selectively variable; and (ii) the positions of the first and second extremes are selectively variable.

11. The apparatus of claim 1 wherein the second unit includes:
    a shaft having a proximal end for operative connection to the second member of the joint replacement device; and
    a hinge unit operable to maintain the shaft in substantially coaxial orientation with respect to a first longitudinal axis passing through a central portion of the articulation surface of the first member of the joint replacement device.

12. The apparatus of claim 11 wherein the hinge unit permits the lateral movement of the first member to move the second member of the joint replacement device such that the shaft is maintained in substantially coaxial orientation with respect to the first longitudinal axis.

13. The apparatus of claim 11 wherein the hinge unit includes:
    a first pivot assembly operable to permit the shaft to rotate about a second longitudinal axis oriented substantially parallel to the shaft; and a second pivot assembly operable to permit the shaft and the first pivot assembly to rotate about a third longitudinal axis oriented substantially parallel to the shaft.

14. The apparatus of claim 1 wherein the second unit includes:
a shaft having a proximal end for operative connection to the second member of the joint replacement device; and
a load unit operable to impart a load on the shaft such that the articulation surfaces of the first and second members of the joint replacement device are in compression.

15. The apparatus of claim 14 wherein the load unit is operable to control the load on the shaft to achieve a substantially constant compressive load as between the articulation surfaces of the first and second members of the joint replacement device.

16. The apparatus of claim 14 wherein the load unit includes:
a drive shaft in alignment with, and coupled to, the shaft and
an actuator coupled to and operable to move the drive shaft such that the drive shaft is biased towards the shaft and imparts the load on the shaft.

17. The apparatus of claim 14 wherein the load unit includes;
a screw shaft in alignment with, and coupled to, the shaft; and
a motor coupled to and operable to rotate the screw shaft within a threaded coupling such that the threaded coupling biases the screw shaft towards the shaft and imparts the load on the shaft.

18. The apparatus of claim 17 wherein the motor is a servo motor that is controlled to variably rotate the screw shaft to achieve a substantially constant compressive load as between the articulation surfaces of the first and second members of the joint replacement device.

19. The apparatus of claim 17 wherein the shaft, the screw shaft and the motor are movable laterally such that the location of the second member of the joint replacement device is automatically adjusted in response to lateral forces exerted by the first member upon the second member.

20. An apparatus for testing components of a joint replacement device in desired articulation relative to one another under a load, comprising:
a first unit operable to impart undulating orientations of a first member of the joint replacement device with respect to a longitudinal axis; the first unit including: a base operable for rotational movement through one or more 360 degree cycles about a first longitudinal axis and having a slanted plane with respect to a first plane substantially perpendicular to the first longitudinal axis; and
an undulating platform coupled to the base for rotation about a second longitudinal axis and oriented in a second plane that is substantially perpendicular to the second longitudinal axis and that is substantially parallel to the slanted plane of the base, the undulating platform being restricted in its ability to rotate about the first longitudinal axis;
a second unit operable to locate a second member of the joint replacement device proximate to the first member of the joint replacement device such that an articulation surface of the second member movingly engages an articulation surface of the first member in response to the undulating orientations of the first member; and
a third unit operable to impart rotational displacement to the first member of the joint replacement device such that the articulation surface of the first member will be engaged with the articulation surface of the second member for the desired articulation of the first and second members.

21. The apparatus of claim 20 wherein:
the rotational movement of the base about the first longitudinal axis causes undulating orientations of the slanted plane and corresponding undulating orientations of the undulating platform by way of its coupling to the base; and
wherein the first member of the joint replacement device is to be coupled to the undulating platform.

22. The apparatus of claim 20 wherein at least one of: (i) a frequency of rotation of the base about the first longitudinal axis is selectively variable; (ii) rotational displacement to which the undulating platform is restricted in its rotation about the first longitudinal axis is selectively variable; and (iii) a frequency of undulation of the undulating platform about the first longitudinal axis is selectively variable.

23. The apparatus of claim 20 further comprising:
a longitudinal race in substantially parallel orientation with respect to the first longitudinal axis; and
an arm extending from the undulating platform into the longitudinal race such that the undulating platform is restricted in its ability to rotate about the first longitudinal axis.

24. The apparatus of claim 23 wherein the arm is operable to move longitudinally within the longitudinal race in response to the undulating orientations of the undulating platform.

25. The apparatus of claim 23 wherein the longitudinal race is operable to move substantially tangentially with respect to the first longitudinal axis to impart rotational displacement to the first member of the joint replacement device about the first longitudinal axis such that the articulation surface of the first member will be engaged with the articulation surface of the second member for the desired articulation of the first and second members.

26. The apparatus of claim 25 wherein the longitudinal race is operable to oscillate between first and second extremes in order to limit the rotational displacement of the first member of the joint replacement device about the first longitudinal axis.

27. The apparatus of claim 26 further comprising an offset crank and a rocker arm coupled between the crank and the longitudinal race to move the longitudinal race substantially tangentially with respect to the first longitudinal axis.

28. The apparatus of claim 26 wherein at least one of: (i) a frequency of oscillation between the first and second extremes is selectively variable; and (ii) the positions of the first and second extremes are selectively variable.

29. A method for testing components of a joint replacement device in desired articulation relative to one another under a load, comprising:
imparting undulating orientations to a first member of the joint replacement device;
locating a second member of the joint replacement device proximate to the first member of the joint replacement device such that an articulation surface of the second member is engaged with an articulation surface of the first member for articulation in response to the undulating orientations of the first member;
automatically adjusting the location of the second member of the joint replacement device relative to the first member in response to lateral forces exerted by the first member upon the second member and thereby attaining the desired articulation;

restricting rotational displacement of the first member about a longitudinal axis of rotation to a frequency of oscillation between first and second extremes, and selecting at least one of (i)the frequency of oscillation and (ii)the location of the first and second extremes relative to one another.

30. The method of claim 29 including imparting a selected load to the second member during articulation of the first and second members.

* * * * *